United States Patent [19]

Daniell, Jr.

[11] 4,312,335
[45] Jan. 26, 1982

[54] CUSTOM-FITTED KNEE GUARD AND BRACE

[76] Inventor: Roy B. Daniell, Jr., 4221 N. Shallowford Rd., Apt. 4, Chamblee, Ga. 30341

[21] Appl. No.: 117,958

[22] Filed: Feb. 4, 1980

Related U.S. Application Data

[63] Continuation-in-part of Ser. No. 896,990, Mar. 17, 1978, Pat. No. 4,233,967.

[51] Int. Cl.³ ............................................. A61F 13/00
[52] U.S. Cl. .................................. 128/80 C; 128/165
[58] Field of Search ............... 128/80 C, 80 F, 87 R, 128/88, 90, 165, DIG. 15; 24/201 R, 230 AP, 230 AS, 241 S, 201 H, 204

[56] References Cited

U.S. PATENT DOCUMENTS

| | | | |
|---|---|---|---|
| 901,592 | 10/1908 | Clegg | 128/88 |
| 1,007,567 | 10/1911 | Holder | 128/88 |
| 2,632,894 | 3/1953 | Louis | 24/204 UX |
| 3,779,654 | 12/1973 | Home | 128/80 C |
| 3,799,158 | 3/1974 | Gardner | 128/80 C |
| 3,817,244 | 6/1974 | Taylor | 128/80 C |
| 3,825,357 | 7/1974 | Hilton | 128/80 F X |
| 3,906,943 | 9/1975 | Arluck | 128/90 |
| 3,958,569 | 5/1976 | Vosburgh | 128/80 C |
| 4,139,002 | 2/1979 | Almedia | 128/88 |
| 4,256,097 | 3/1981 | Willis | 128/80 F |

OTHER PUBLICATIONS

The "Nature and Properties of Engineering Materials", 2nd Edition, Zbigniew D. Jastrzebski, John Wiley & Sons, New York, 1976, Chart A4, "Structures and Properties of Thermo Plastics".

Primary Examiner—Robert W. Michell
Assistant Examiner—J. L. Kruter
Attorney, Agent, or Firm—Vivian L. Leon; Harry I. Leon

[57] ABSTRACT

A knee guard and brace having bilaterally symmetrical, semi-rigid thigh and calf encasements for the protection of the knee area from the thigh to the calf. The device, other than padding and retaining screws, is made entirely of a thermoplastic material by an injection molding process. Ribs which run parallel to a wearer's leg are pivotally interconnected at the side of the knee joint. Stress on each screw which retains the end portions of a pair of ribs in overlapping engagement at a pivotal joint is reduced by the use of a shoulder and of a groove and ring projection, the groove being concentric with the shoulder in one of the ribs and being slidably engaged with the ring projection which protrudes from the contiguous face of the other rib. Sections of the ribs which are disposed above and below the knee joint area are embedded in the thigh and calf encasements, respectively. On either side of a pivotal joint, the juncture of each rib with an encasement is strengthened by means of a reinforcing abutment. The embedded rib sections are tapered, the taper decreasing in the direction away from the pivotal joint. The weight of the ribs is further reduced, without loss in the overall strength of the device, by recessing a portion of each tapered rib section. The encasements are secured to a wearer's leg by means of straps, the encasements having flanges in which holes are molded so that the flanges can be seated over studs which are molded in the straps.

8 Claims, 10 Drawing Figures

FIG. 4
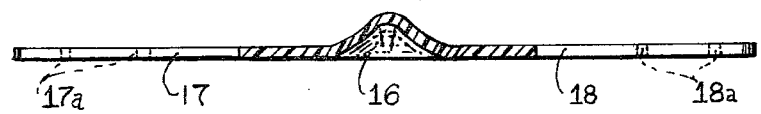
FIG. 5
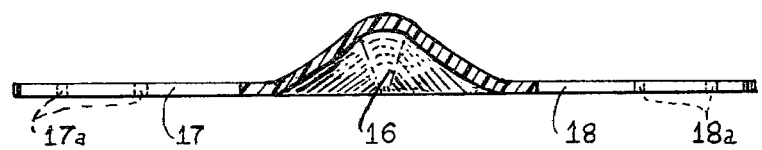
FIG. 6
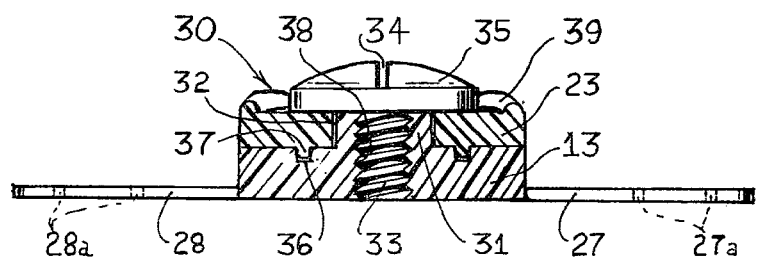
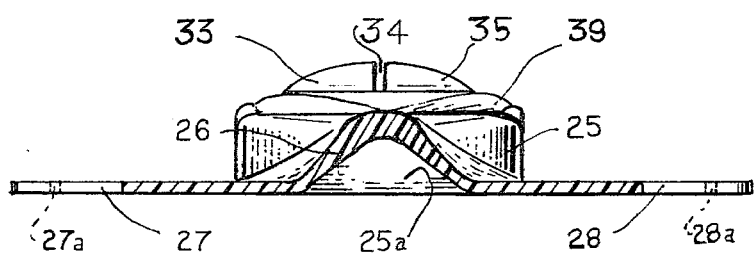
FIG. 7

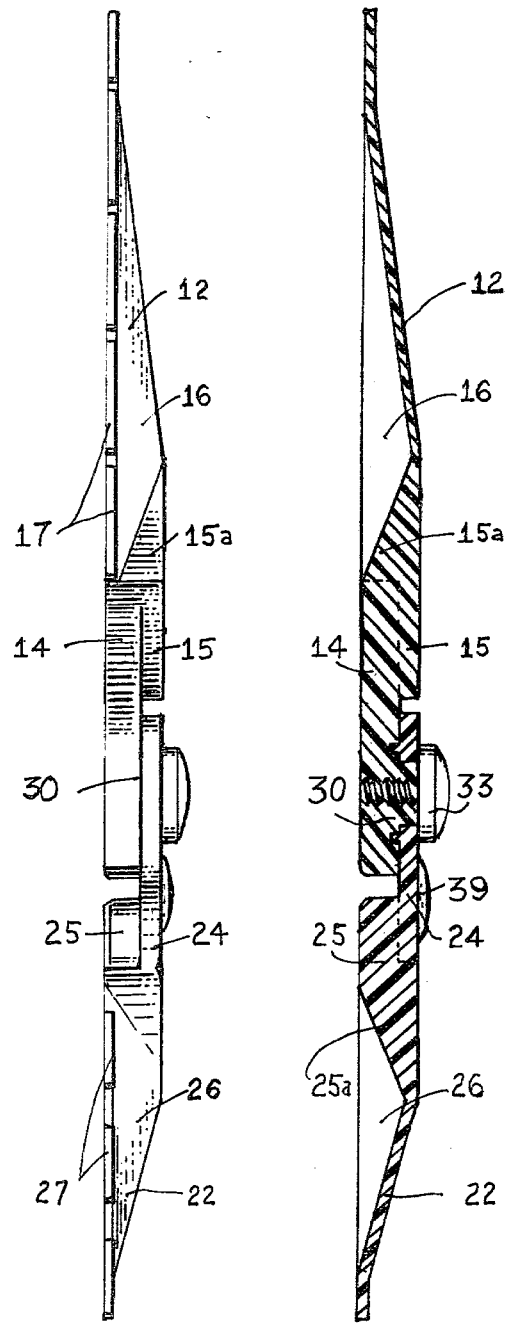
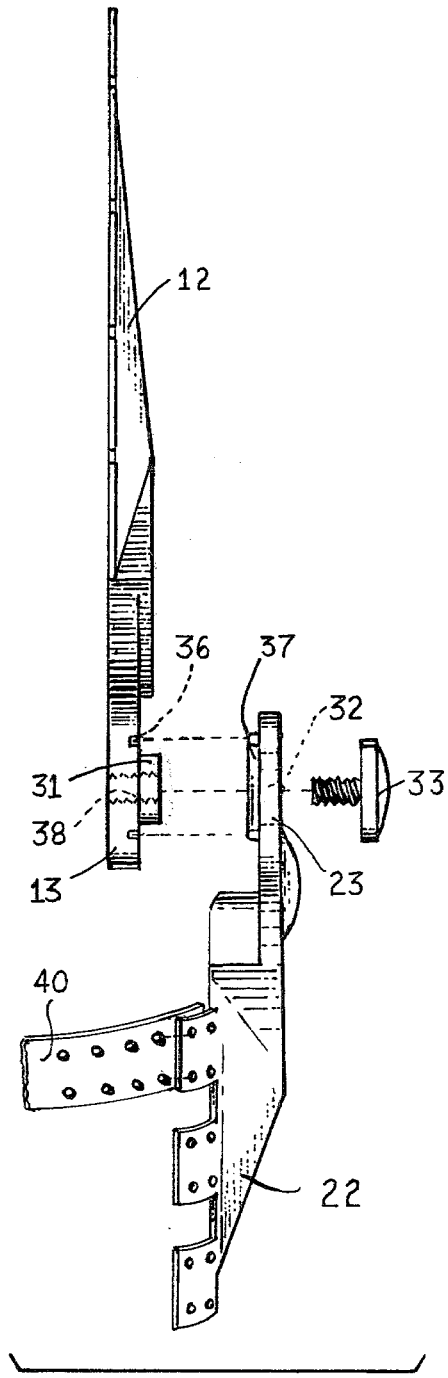
FIG. 8    FIG. 9    FIG. 10

CUSTOM-FITTED KNEE GUARD AND BRACE

CROSS-REFERENCE TO RELATED APPLICATION

This application is a continuation-in-part of application, Ser. No. 896,990, filed Mar. 17, 1978, now U.S. Pat. No. 4,233,967.

BACKGROUND OF THE INVENTION

1. Field of the Invention

The present invention relates generally to knee guards and braces and more particularly to such devices for reducing the chance of injury and the extent of damage to the knee area which an athlete may incur during contact sports and to give aid and support in the rehabilitation of a knee or leg injury.

2. Description of the Prior Art

The principal injury to the leg of an athlete incurred in contact sports develops from a blow to or a twist in the knee area. Knee guards and braces with metal ribs of the prior art tend to be heavy, bulky, time-consuming to affix, uncomfortable to wear, and short-lived. Because of these inherent problems, athletes are forced to wear these devices only after an injury to a leg and not before such injury.

The lightweight braces of the prior art, on the other hand, which by and large are tubes of elastic with longitudinal strips of plastic or thin metal for support on both sides of the knee, cannot withstand a strong lateral blow or a twisting of the knee. Rather such lightweight braces were designed as a support in a therapeutic manner. Moreover, efforts to form strong pivotal joints between plastic support strips or ribs were hampered in part because of the impracticality of forming molded plastic parts with chosen tolerances.

In my patent identified above, there has been disclosed a lightweight, but unusually strong knee guard and brace made entirely of a plastic material. This device comprises four support members; each of the two support members adapted to fit on the outside of a wearer's leg has a rib, flanges, and straps which comprise a single, unitary piece formed of plastic. Similarly, each of the two support members adapted to fit on the inside of a wearer's leg has a rib and flanges which comprise a single, unitary piece formed of plastic. A recess in the flanged portion of each rib is provided to reduce the overall weight of the knee guard and brace. In order to reduce the likelihood of the collapse of the pivotal joint under the force of a lateral blow or from the stress of torsional twisting, portions of the rib at the side of the joint are structurally strengthened. In the patent identified above, the applicant disclosed a curvature in each rib at the side of the pivotal joint away from the surface of a wearer's leg, the curved ribs forming an arch over the knee joint when they are pivotally interconnected.

SUMMARY OF THE INVENTION

The subject invention is directed to improvements over applicant's prior teachings by way of a reinforcing abutment which forms a lap joint between the bridging section of each rib and the flanged portion thereof. Each reinforcing abutment has a decreasing taper both in width and in thickness in a direction away from the proximate edges of the flanges and toward the distal edge of the support member. The reinforcing abutments so tapered provide adequate strength to the ribs so that the force of a lateral blow taken in the vicinity of the pivotal joint can be dissipated to the large muscles of a wearer's leg rather than absorbed at the knee joint. Further, the reinforcing abutments strengthen the ribs so that they can withstand a torsional twisting of the encasements in which the ends of the ribs are embedded relative to each other. In each support member, the rib, the reinforcing abutment, and the flanges comprise a single, unitary piece formed of plastic.

The additional weight of the reinforcing abutments is counterbalanced by a reduction in the weight of the recessed portion of each rib, each rib having a decreasing taper in a direction toward the distal edge of the support member and away from the reinforcing abutment. Since the rib is progressively narrower in those sections of the support member which dissipate a progressively lower percentage of the force of a blow received at the pivotal joint, the reduction in the size of the rib does not diminish the overall strength of the knee guard and brace.

A further improvement is in the strenghtening of the pivotal joint itself. The inclusion of a circular groove in the overlapping end portion of one of the ribs which is slidably engaged with a ring projection in the other rib when the two ribs are pivotally interconnected provides a means for transmitting a large percentage of the force of a blow received at the pivotal joint away from the retaining screw.

A neck in the middle of each bridging section has been provided to reduce the chance of pinching any fingers which may enter the narrow space formed between the edges of the two bridging sections of a side member when a wearer's knee is bent. Further, the proximate edges of the reinforcing abutments have a decreasing taper in a direction away from the proximate edges of the flanges. The latter taper eliminates interference between the movements of the bridging section of one rib and the reinforcing abutment on the other rib during the bending of a wearer's knee.

A further improvement is the provision of a pair of symmetrical side members so that both members can be fabricated independently in the same injection molding die, significantly reducing manufacturing costs. In each symmetrical side member, the flanges have a plurality of pairs of holes; and the straps which connect one side member to the other have a plurality of studs. The placement of the studs on the straps allows one to align the holes in the flanges with an equal number of studs in the contiguous portions of the straps, so that the flanges can be seated over the studs, securing the knee guard and brace and encasing a wearer's leg above and below the knee.

Thus the present invention provides a lightweight, but extremely strong and less cumbersome knee guard and brace which can be used by most athletes participating in contact sports to reduce the chance of injuries from side or lateral blows to the knees and from torsional twisting of the legs.

A further object of one embodiment of this invention is to provide a lightweight, but strong supportive and protective apparatus for use by orthopedic patients in need of knee or leg bracing.

Other objects and advantages will appear from the following description of an example of the invention, when considered in connection with the accompanying drawing, and the novel features will be particularly pointed out in the appended claims.

BRIEF DESCRIPTION OF THE DRAWINGS

FIGS. 4, 5, 6, and 7 are cross-sectional views taken on lines IV—IV, V—V, VI—VI, and VII—VII, respectively, of FIG. 2 on an enlarged scale.

FIG. 8 is a side elevational view of the side member of a knee guard and brace seen from the left side of FIG. 2.

FIG. 9 is a cross-sectional view taken on line IX—IX of FIG. 3.

FIG. 10 is an exploded view showing in perspective several of the side member parts shown in assembled form in FIG. 8 and the end portion of one of the straps which connect the side members to each other.

Like reference characters indicate corresponding parts throughout the several views of the drawings.

DESCRIPTION OF THE PREFERRED EMBODIMENT

Figure 1:
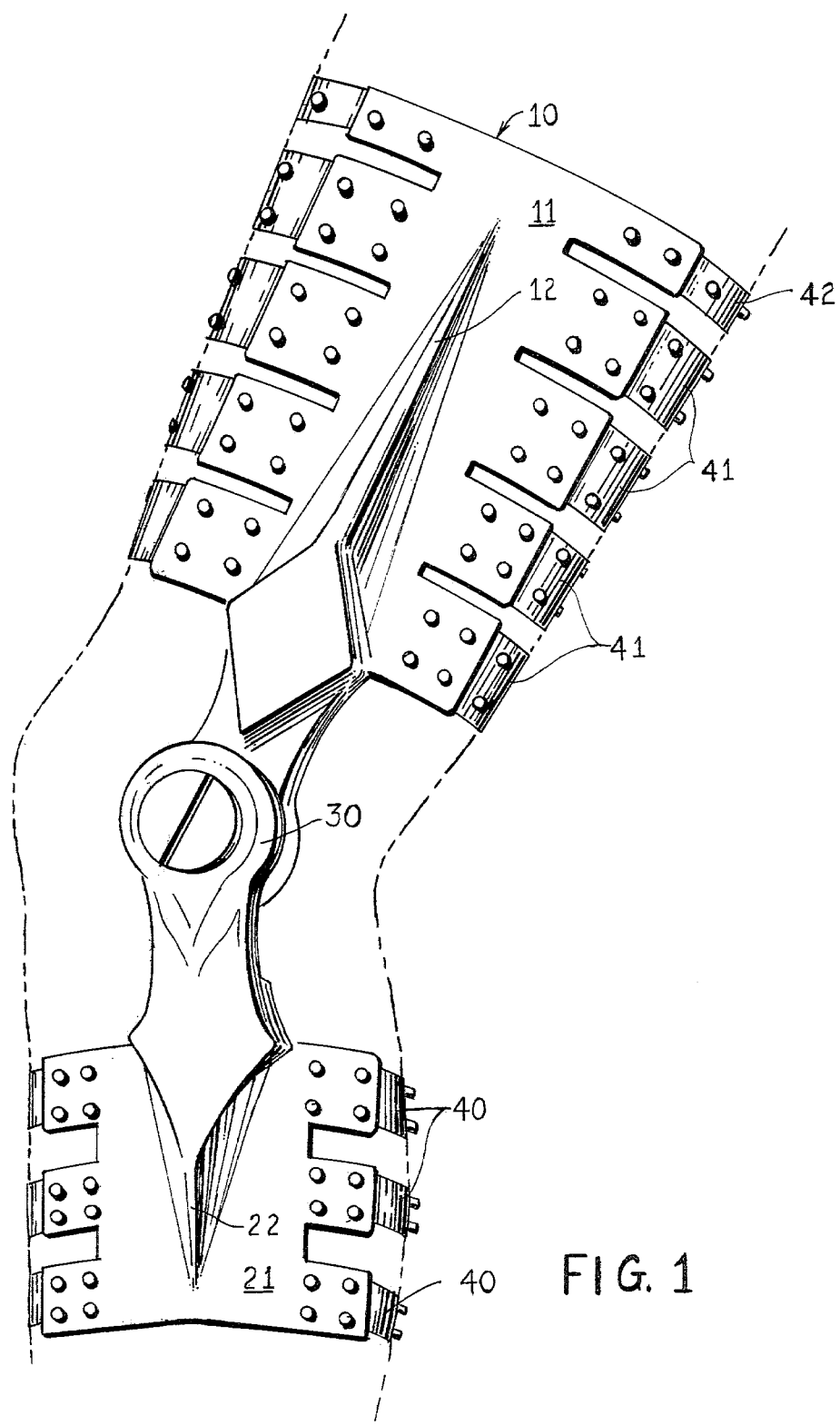
FIG. 1 is a perspective view of a knee guard and brace incorporating the present invention attached to the outer side of the left leg of a wearer.

Referring to FIG. 1 of the drawings, a side member 10 of a knee guard and brace, incorporating the present invention, is shown attached to the outer side of a wearer's left leg. Each knee guard and brace comprises a pair of side members 10. One of the side members is adapted to fit on the inside of a wearer's leg and the other on the outside of the leg. Each side member 10 has two parts: a lower thigh support member 11 and an upper calf support member 21 which are interconnected pivotally at the joint 30.

Figures 2, 3:
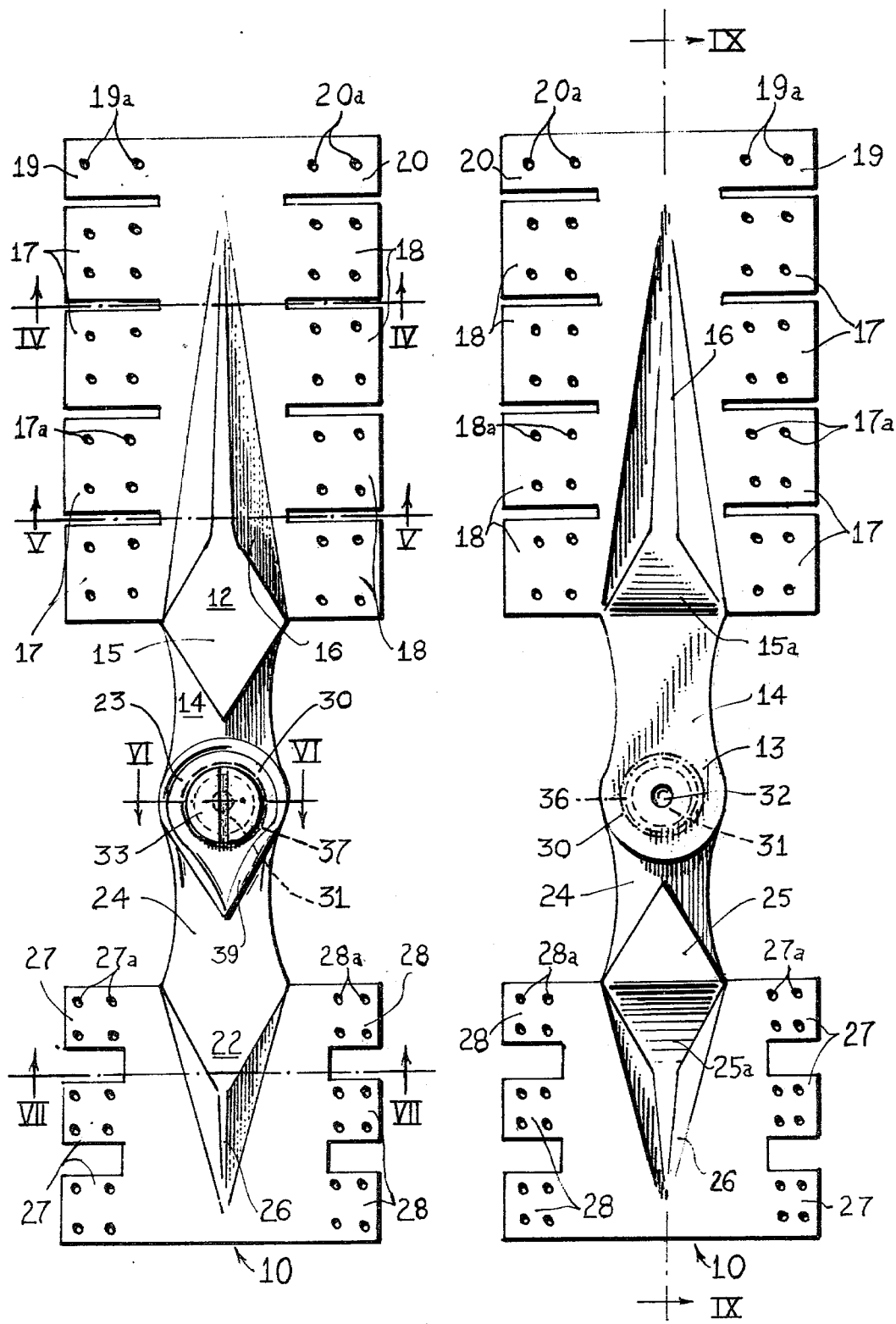
FIGS. 2 and 3 are reduced frontal and rear elevational views, respectively, of the side member of a knee guard and brace according to the present invention.

Each side member 10 has two pivotally-connected ribs 12 and 22 which together longitudinally span the area of the knee joint at the side of the knee cap. As is best seen in FIGS. 2 and 3, opposite sides of the ribs have flanges 17-20 and 27-28 above and below the knee area. A recess is formed in each rib, the recessed portions 16 and 26 of the ribs being disposed within the flanges portions thereof and contiguous of the wearer's skin.

Each side member 10 is attached to the wearer's thigh and calf and held in place relative to the other member by means of straps and studs. As seen in FIG. 1, the straps extend laterally around the leg connecting the upper flanges to each other and the lower flanges to each other so that the knee guard and brace forms a pair of upper and lower encasements which can be fitted to a wearer's leg above and below the knee cap.

By having side members 10 on either side of the knee joint, the chance of the pivotal joint 30 collapsing from either a lateral blow to the joint itself or a torsional twisting of the leg is greatly reduced. When a blow is received laterally from the outside, the side member 10 adapted to fit on the inside of a wearer's leg is taut against the knee, reducing the chance of collapse. The inside member is held taut against the knee by the plurality of straps binding it to the outside member.

The likelihood of a failure of the knee guard and brace under torsional twisting is further reduced by embedding the end of each rib in the encasement to which it is connected, the rib and the flanges which extend laterally therefrom comprising a single, unitary piece formed of plastic. The movement of the wearer's leg relative to the encasements is minimized in two ways. First, the straps are connected to the flanges by means of studs. Secondly, the support members adapted to fit on the outside of a wearer's leg are shaped to the wearer's thigh and calf contours during a molding process.

The molding for shaping to the leg contour is simply performed by heating the wafer thin plastic of less than 1/16th inch thickness in the outer skin of the support members to a pliable state. Once this skin has reached a temperature of approximately 300° F., the support members are placed over a heat-protected leg; and the plastic therein is allowed to form quickly and to cool quickly. The molded outside member is then secured by means of straps to the inside member. Once the plastic material becomes semi-rigid, the device with encasements so fitted inhibits unnecessary torsional movement of the wearer's leg.

The knee guard and brace as thus far described follows the teachings of application Ser. No. 896,990, filed Mar. 17, 1978, now U.S. Pat. No. 4,233,967.

In accordance with the present invention, there is provided improved means for dissipating the force of a lateral blow received in the pivotal joint area away from the joint to the large muscles of a wearer's leg and of transmitting forces arising from the torsional twisting of a wearer's leg around the pivotal joint 30. Thus, as shown in FIGS. 2, 3, and 8, there is provided a reinforcing abutment 15 which forms a lap joint between the bridging section 14 and the recessed portion 16 of the rib 12. Similarly, a reinforcing abutment 25 joins the bridging section 24 and the recessed portion 26 of the rib 22. As seen in FIG. 2, a portion of the abutment 15 which is formed on the outer surface of the rib 12 and away from a wearer's skin has a decreasing taper in the longitudinal direction away from the proximate edges of the flanges and towards the pivotal joint 30. Correspondingly, a portion of the abutment 25 formed on the inner surface of the rib 22 and contiguous to a wearer's skin has a similar decreasing taper in width in the longitudinal direction. As seen in FIG. 9, the thickness of each rib is greatest in those cross-sections of the rib in which the reinforcing abutment and the bridging section are joined. To reinforce the thinner bridging section 24, ridges 39 which protrude from the outer surface of the rib 22 in and near the pivotal joint are also provided. The dashed lines in FIG. 9 show the points at which the outer and inner surfaces of the bridging members interface with the tapered edges of the reinforcing abutments. As is shown in FIGS. 2, 3, 7, and 9, each reinforcing abutment also has a decreasing taper both in width and in thickness away from the proximate edges of the flanges and toward the distal edge of the support member. The portions of the reinforcing abutments having this decreasing taper in two dimensions, that is, tapered portions 15a and 25a, are joined to the recessed portions 16 and 26 which are also tapered in two dimensions as see in FIGS. 2-5, 7-9. The reinforcing abutments and recessed portions of the ribs so tapered provide adequate strength to the ribs so that the force of a lateral blow taken in the vicinity of the pivotal joint 30 ca be dissipated to the large muscles of a wearer's leg rather than absorbed at the knee joint. Further, the reinforcing abutments strengthen the ribs so that they can withstand a torsional twisting of the encasements in which the ends of the ribs are embedded upon a torsional twisting of a wearer's leg. Since the rib, the reinforcing abutment, and the flangers in each support member comprise a single, unitary piece, even differential movement between the rib and the points of attachment of the knee guard and brace to a wearer's leg is minimized in this invention.

A neck in the middle of each bridging section 14 and 24 (see FIGS. 2 and 3) has been provided to reduce the chance of pinching any fingers which may enter the narrow space formed between the edges of the two bridging sections when a wearer's leg is bent. Further, the taper in the reinforcing abutments 15 and 25 along the edges thereof which are contiguous with the briding sections 14 and 24 both reduces the weight of the knee guard and brace and eliminates interference between the movements of the bridging section of one rib and the reinforcing abutment on the other rib during the bending of a wearer's knee.

As is best shown in FIGS. 6 and 10, the overlapping end portion 13 has a shoulder 31 with internal threads 38 which is inserted into a hole 32 formed in the overlapping end portion 23. The shoulder 31 is fabricated together with the end portion 13 in one injection operation; and the shoulder 31 and the end portion 13 comprise a single, unitary piece formed of plastic. The shoulder 31 and the end portions 13 and 23 are held in assembled relation by a retaining means such as a screw 33.

The head 35 of the retaining screw 33 is enlarged so that forces on the screw are dissipated to a larger surface area of the end portion 23. The use of a screw with an enlarged head is preferred over the use of a snap ring as described in my patent identified above because such a screw allows flexibility in adjusting the tightness of the pivotal joint 30 between the end portions 13 and 23. This tighter fit increases the likelihood that both end portions will bend as one unit, rather than independently of each other, under the stress of a lateral blow or of a torsional twisting of the wearer's leg, thereby reducing the chance that the joint will collapsce from such a stress. The combination of the two end portions bending as one unit and of the reinforcing abutments joining each rib to the flanged portions thereof functions in a manner similar to the arch described in my patent identified above.

The shoulder 31, rather than the screw 33, rubs against the sides of the hole 32 reducing the chance that the screw will become loosened in use. A slot 34 is provided in the screw head 35 to facilitate tightening or loosening the screw by means of a large coin or screwdriver.

The diameter of the hole 32 is slightly larger than the diameter of the shoulder 31 allowing for clearance. The diameter of the shoulder 31 is approximately twice the diameter of the screw 33, the thickness of the shoulder allowing it to withstand greater stresses that the screw alone could withstand.

A circular groove 36 concentric with the shoulder 31 is provided in the end portion 13 (see FIGS. 2, 3, 6, and 10). A ring projection 37 concentric with the hole 32 formed in the contiguous face of the overlapping end portion 23 slides in the groove 36 when the pivotally-interconnected ribs 12 and 22 move relative to each other. The groove and ring projection are provided to further reduce shear forces on the screw 33. For this purpose, a relatively close tolerance between the side of the ring projection having a greater diameter and the side of the groove contiguous thereto is desirable. A clearance on the order of a few 1/1000ths of an inch which still allows sliding contact between the outer sides of the ring projection and the groove is preferred.

The clearance between the inner sides of the ring projection and groove is preferably equal to or somewhat larger than that between the outer sides, so that the outer sides of the ring projection and of the groove serve as the primary structure for reducing shear forces on the screw 33. The less tightly fitting shoulder 31 and hole 32, on the other hand, provide the secondary structure for reducing these shear forces. That is, in the case of less severe forces, the ring projection and groove combination dissipates most of the force; in the case of more severe forces, the shoulder dissipates a larger share of the force away from the screw. The ring projection is of sufficient width, being approximately 1/8th inch in cross-section, to withstand the shearing loads which may be applied to it.

The top of the ring projection 37 is rounded and does not necessarily contact the bottom surface of the groove 36. Rather the remainder of the contiguous faces of the end portions 13 and 23 function as large, self-lubricating bearing surfaces for the pivotal joint 30. The outer edges of these bearing surfaces are rounded, defining a circle concentric with the center of rotation as seen in FIGS. 2 and 3. The use of such curved surfaces both in the overlapping end portions and in the bridging sections avoids the unnecessary inclusion of stress points which might awaken the knee guard and brace.

The shoulder 31 also serves to prevent one from overtightening the screw 33. The shoulder, being a few 1/1000ths of an inch above the outer surface of the end portion 23, rather than the end portion 23 takes most of the load from tightening the screw 33, thereby reducing the chance that the screw will become loose with the rotation of the end portion 23.

In the present invention, the side members 10 which are adapted to fit either on the outside of a wearer's leg or on the inside of a wearer's leg are fabricated in the same injection molding die, thus eliminating manufacturing costs for a second asymmetrical side member. The flanges 17–20 and 27–28 in the support members have a plurality of pairs of holes 17a–20a and 27a–28a (see FIGS. 2 and 3) formed therein. The upper flanges of the side members and the lower flanges of the side members are connected to each other by means of studded straps 40–42 (see FIGS. 1 and 10). The interval separating two studs from each other in a lateral direction in a strap is equal to the interval separating each pair of holes in the same direction or a multiple thereof. The holes can be aligned with an equal number of studs in the contiguous portions of the straps; and the studs have the same diameter at the interface between the studs and flanges as the diameter of the holes. Thus the flanges can be seated over the studs, securing the knee guard and brace and substantially encasing a wearer's leg in a cumstom-moldable, thermoplastic material above and below the knee.

What is claimed is:

1. A knee guard and brace, which comprises:
    (a) inside and outside members which are adapted to fit on the inner and outer sides, respectively, of a wearer's leg; each side member comprising a pair of thigh and calf support members;
    (b) each support member having a rib with end portions, the rib being disposed parallel to the wearer's leg;
    (c) means pivotally interconnecting the end portions of the ribs in overlapping engagement, so that the pair of ribs when interconnected form a bridge over the side of the knee joint;

(d) each support member having at least two flanges which extend laterally from opposite sides of the rib and to the distal edges thereof, the flanges being wholly disposed within the portions of the thigh and calf support members which are located above and below the knee joint, respectively; each rib and the flanges which extend laterally therefrom comprising a single, unitary piece formed of a thermoplastic material;

(e) each rib having a bridging section disposed between the overlapping end portion of the rib and the proximate edges of the flanges;

(f) a reinforcing abutment joining the bridging section of each rib to the flanged portion thereof, the thickness of each rib in a direction generally perpendicular to the contiguous surface of a wearer's leg being substantially greater in those portions thereof in which the reinforcing abutment is joined to the bridging section than in the remainder of the bridging section, thereby facilitating the transmission of loads away from the pivotal joint and to the large muscles of a wearer's leg; the abutment having a taper both in width and in thickness in a direction away from the proximate edges of the flanges and toward the distal edges of the support member; and (g) a plurality of straps connecting the upper flanges to each other and the lower flanges to each other, so that the knee guard and brace forms a pair of upper and lower encasements which can be fitted to a wearer's leg above and below the knee and which, in combination with the interconnected end portions of the ribs, inhibit torsional twisting of the wearer's leg.

2. A knee guard and brace according to claim 1 wherein the pivotal means further comprises:

(a) a means for retaining the overlapping end portions in assembled relation;

(b) one of the overlapping end portions having a shallow, circular groove of channel-shaped cross-section; and (c) the other overlapping end portion having an annular ring projection of approximately hemispherical cross-section in a direction radial to the pivotal center, the outer side of the ring projection being slidably engaged with the groove when the end portions of the ribs are pivotally interconnected in overlapping engagement, thereby substantially reducing shear forces on the retention means without simultaneously increasing the lateral bearing surface area significantly.

3. A knee guard and brace according to claim 1 wherein (a) the reinforcing abutment joined to the bridging section of the rib in the thigh support member projects generally in the opposite direction from that of the reinforcing abutment joined to the bridging section of the rib in the calf support member;

(b) the combined thickness of the transverse cross-sections of the overlapping end portions of the ribs when they are pivotally interconnected is at least as great as the thickness of the transverse cross-section of each portion of each rib in which the reinforcing abutment and the bridging section are joined; and (c) a portion of each rib extending from the distal edges of the reinforcing abutment joined thereto is tapered from wide to narrow in a direction toward the distal edge of the support member, so that the thicker portions of each side member are disposed substantially within one of the concave regions of a wearer's knee joint which are formed on either side of the knee cap.

4. A knee guard and brace according to claim 1 wherein each rib forms a recess contiguous to the wearer's skin, the recess being tapered from wide to narrow in a direction toward the distal edge of the support member.

5. A knee guard and brace according to claim 1 further comprising the flanges having a plurality of pairs of holes; and the straps having a plurality of studs attached thereto, the interval separating the studs from each other in a lateral direction being equal to the interval separating the holes in the same direction or a multiple thereof; the holes being aligned with an equal number of studs in the contiguous portions of the straps, and the studs having the same diameter at the interface between the studs and the flanges as the diameter of the holes, so that the flanges can be seated over the studs, securing the knee guard and brace and substantially encasing a wearer's leg above and below the knee.

6. A knee guard and brace according to claim 1 wherein (a) the pivotal means further comprises a shoulder projecting from one of the contiguous faces of the overlapping end portions; the end portion of the rib in overlapping engagement therewith having a hole through which the shoulder is inserted; the shoulder having a retention means for maintaining the overlapping end portions in assembled relation;

(d) one of the overlapping end portions has a circular groove; and (e) the other overlapping end portion has a ring protection, the ring projection being slidably engaged with the groove when the end portions of the ribs are pivotally interconnected, the portions of the grooves which are proximate the shoulder being spaced therefrom, thereby keeping the shoulder centered within the hole during rotational motion of the ribs and substantially reducing shear forces on the retention means.

7. A knee guard and brace according to claim 6 wherein the width of the transverse cross-section of each of the overlapping end portions is substantially greater than the combinated width of the groove and the diameter of the shoulder, so that loads on the pivotal joint can be partially distributed through those portions of the rib which surround the groove and the shoulder.

8. A knee guard and brace, which comprises:

(a) inside and outside members which are adapted to fit on the inner and outer sides, respectively, of a wearer's leg; each side member comprising a pair of thigh and calf support members;

(b) each support member having a rib which runs parallel to the wearer's leg;

(c) means pivotally interconnecting the end portions of the ribs in overlapping engagement, so that the pair of ribs when interconnected form a bridge over the side of the knee joint;

(d) each support member having at least two flanges which extend laterally from opposite sides of the rib, the flanges being wholly disposed within the portions of the thigh and calf support members which are located above and below the knee joint, respectively;

(e) each rib having a bridging section disposed between the overlapping end portion of the rib and the proximate edges of the flanges; ;p1 (f) a reinforcing abutment joining the bridging section of each rib to the flanged portion thereof, the thickness of each rib in a direction generally perpendicular to the contiguous surface of a wearer's leg being substantially greater in those portions thereof in which the reinforcing abutment is joined to the bridging section than in the remainder of the bridging section, thereby facilitating the transmission of loads away from the pivotal joint and to the large muscles of a wearer's leg; the abutment having a taper both in width and in thickness in a direction away from the proximate edges of the flanges and toward the distal edges of the support member;

(g) the reinforcing abutment joined to the bridging section of the rib in the thigh support member projecting generally in the opposite direction from that of the reinforcing abutment joined to the bridging section of the rib in the calf support member; the edges of each reinforcing abutment which are proximate to each pivotal joint, having a taper in a direction away from the proximate edges of the flanges and toward the pivotal joint, thereby eliminating interference between the movements of the bridging section of one rib and the reinforcing abutment of the other rib; and (h) a plurality of straps connecting the upper flanges to each other and the lower flanges to each other, so that the knee guard and brace forms a pair of upper and lower encasements which can be fitted to a wearer's leg above and below the knee and which, in combination with the interconnected end portions of the ribs, inhibit torsional twisting of the wearer's leg.

* * * * *